United States Patent [19]

Visser

[11] Patent Number: Plant 6,450

[45] Date of Patent: Dec. 6, 1988

[54] ELSTAR APPLE TREE

[75] Inventor: Tijs Visser, Wageningen, Netherlands

[73] Assignee: Instituut voor de Veredeling van Tuinbouwgwassen, Wageningen, Netherlands

[21] Appl. No.: 8,765

[22] Filed: Jan. 30, 1987

[51] Int. Cl.[4] ..... A01H 5/03

[52] U.S. Cl. ..... Plt./34

[58] Field of Search ..... Plt./34

*Primary Examiner*—Robert E. Bagwill

*Attorney, Agent, or Firm*—Chernoff, Vilhauer, McClung & Stenzel

[57] ABSTRACT

A new variety of apple selected from a seedling population, characterized by the taste, flavor and aroma of its dessert quality fruits which have good storageability and by its dense bushy foliage.

2 Drawing Sheets

BACKGROUND AND SUMMARY OF THE INVENTION

This invention relates to a new and distinct variety of apple tree which was selected from a population of seedlings resulting from known crosses of Golden Delicious apple (unpatented and the seed parent) and Ingrid Marie (unpatented and the pollen parent). The crosses were made in 1955 by Dr. T. Visser at the Institute for Horticultural Plant Breeding, Mansholtlaan 15, Wageningen, Netherlands.

The new seedling variety first fruited in 1963 and was selected for propagation and further testing in 1965. It since has been recognized and selected as a new and improved apple variety which is distinctive from its parents as well as from all other apple varieties. It possesses several unusual and commercially desirable characteristics as set forth below:

1. A very high quality dessert fruit embracing the best dessert characteristics of both its parents. It possesses a distinctive taste and fruity aroma plus creamy-white flesh which is solid and juicy. It is suitable for eating fresh and for baking and salads. It is unsuitable for processing into juices and sauce.

2. A regular and annual bearing habit which differs from its Golden Delicious seed parent but is similar to its pollen parent, the Ingrid Marie variety.

3. A dense foliage, bushy characteristic of growth that continues late into the season and possesses leaves that remain on the tree relatively late into Autumn. In this respect it differs distinctly from its seed parent but less so from its pollen parent.

4. A primary shoot-growth characteristic that often produces two or three new smaller shoots at their apex. The new seedling variety differs from both of its parents in this unique growth characteristic.

5. A fruit form, shape and size (roundish, conic, broad, about 3 to 3¼ inch diameter (similar to its pollen parent the Ingrid Marie variety but different from its seed parent the Golden Delicious variety).

6. Fruit with a distinctive and attractive golden-yellow ground color overlaid with bright-red stripes which coalesce into an overall red color as the season progresses.

7. A tree growth character more vigorous and branching more freely than either of its parent varieties.

8. A good-keeping (long storage life) apple similar in this respect to both of its parent varieties.

9. A fruit stock stem similar to its pollen parent but differing from its seed parent.

The new seedling variety has been reproduced asexually by budding and grafting. All subsequent asexually produced generations have been true to form in both their growth and fruiting characteristics and show that the foregoing characteristics come true and are established and transmitted through succeeding propagations and generations.

DETAILED DESCRIPTION OF THE INVENTION

Figure 1:
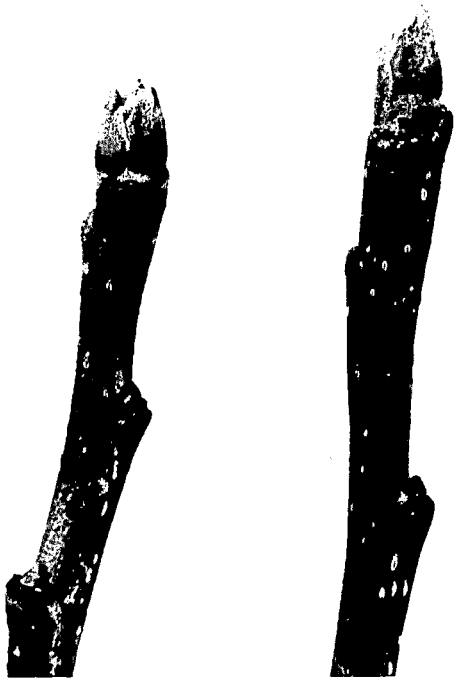
FIG. 1 shows the twigs of the new variety and the reddish coloration of the terminal buds in late Autumn.
Figure 2:
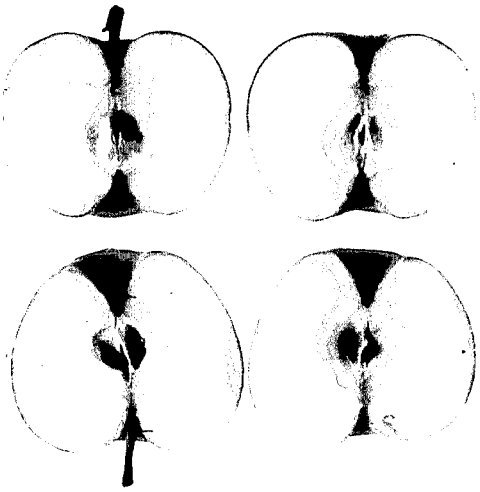
FIG. 2 is a longitudinal section of the fruit grown in the new variety with seeds in place.
Figure 3:
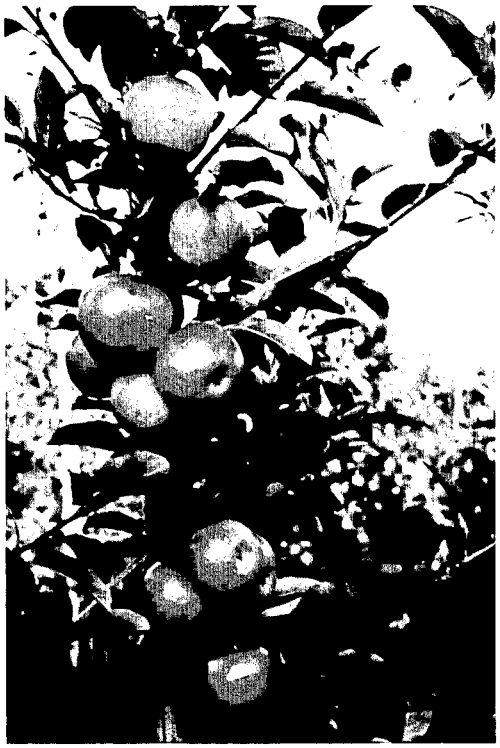
FIG. 3 shows young trees in the third growing season on M-9 rootstock.
Figure 4:
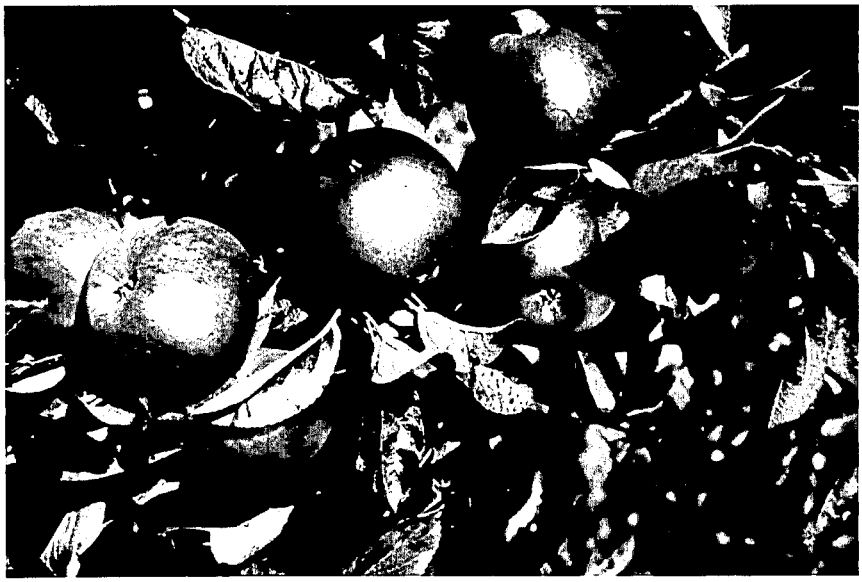
FIG. 4 is a close-up of fruit grown on the new variety.

The following is a detailed description of the new apple variety with color terminology in accordance with the *Munsell Color Cascade Chart* except where general color terms of ordinary dictionary significance are used.

Parentage: A cross of "Golden Delicious" and "Ingrid Marie" apple varieties.

Locality where grown and observed: Mt. Vernon and Yakima, Wash. and Dayton, Ore.

Dates of first and last pickings: About September 30, and October 15, respectively.

Tree: Medium to large, vigorous, slightly bushy with dense foliage, growth continues until late into season.

*Trunk.*—Medium stocky, smooth.

*Branches.*—Medium thick, smooth, much branched. Color — Green-brown (22-14).

*Twigs.*—Slender. Lenticels — Numerous, medium large, white. Color — Grey with reddish terminal buds.

Leaves: Medium large, medium wide, medium long, oval, abruptly pointed, medium thick, smooth.

*Length.*—3¾ inches to 4¼ inches.

*Width.*—1⅝ inches to 2⅛ inches.

*Color.*—Green (20-12).

*Margin.*—Finely serrate, crenate.

*Petiole.*—Long ($1\frac{1}{8}$ inch to $1\frac{3}{8}$ inch), medium slender.

*Pose.*—Upward.

Flowers: Late.

*Date of first and full bloom.*—About April 15 and April 25, respectively.

*Size.*—Medium large.

*Color.*—Pinkish-red (43-6).

Fruit:

*Maturity when described.*—Eating ripe.

*Size.*—Uniform. Axial diameter — About $2\frac{3}{4}$ inches to 3 inches. Transverse diameter — About 3 inches to $3\frac{1}{4}$ inches.

*Form.*—Conic to slightly oblong, broad, rounded at base, side usually slightly unequal.

*Cavity.*—Acute, medium width, medium depth, symmetrical, greenish russet (unbroken).

*Basin.*—Abrupt, symmetrical, regular to slightly wavy, medium width, medium depth. Markings — None.

*Stem.*—Short, thick, somewhat fleshy, not lipped, slightly clubbed. Length — $\frac{3}{8}$ inch to $\frac{1}{2}$ inch. Breadth — about 3/16 inch.

*Calyx.*—Partly open, calyx lobes persist and separated at base. Calyx lobes — Reflexed and divergent. Pubescence — None.

*Skin.*—Slightly rough, tendency toward thin russet. Stem cavity — Greenish unbroken russet. Dots — Inconspicuous, small, scattered at base, numerous toward apex, roundish. Suture — None. Color — Yellow-orange ground color (31-9), overlaid with short, narrow, mostly broken red stripes and splashes of red (39-12). Scarfskin — Greenish scarfskin present. General color effect — Short, narrow, bright red stripes over orange colored ground.

*Flesh.*—Juicy, solid. Color — Creamy-white tinged with yellow. Texture — Firm, fine, tender, crisp. Flavor — Sub acid to sweet. Aroma — Distinct, fruity. Quality — Best.

*Core.*—Median. Bundle area — Medium small, symmetrical. Halves of area — Equal. Bundles — Inconspicuous. Core lines — Meeting, heartshaped. Cross section — Indistinct. Calyx tube — Funnel-form, glabrous toward base. Stem (cylinder) of funnel — Medium long. Depth of tube to shoulder — About 3/16 inch. Entire depth — About $\frac{1}{2}$ inch. Styles — Present, united at base. Stamens — Median, in one whorl. Seed calls (Carpels) — Axile, open, symmetrical, smooth, heartshaped (Cordate form), emarginate at outer edge near tip.

Other characteristics:

*Seeds.*—One or two per cell, not tufted, acute at point, 5/16 to $\frac{3}{8}$ inch long, 3/16 inch wide, obtuse, dark brown (31-15).

*Use.*—Dessert, market.

*Keeping quality.*—Very good, but has tendency to lose aroma and good taste following excessively long storage (beyond six months).

*Disease susceptibility.*—Average for scab and mildew, susceptible to common viruses, virus-tested budwood available for propagation.

*Winter hardiness.*—Slightly less than its Golden Delicious seed parent.

*Precosity.*—Similar to its Golden Delicious seed parent.

*Fertility.*—Similar to its Golden Delicious seed parent. Crops best with cross-pollination.

What is claimed is:

1. A new variety of apple tree substantially as shown and described herein characterized by its high quality dessert type fruit which possesses an appealing, rich, fruity aroma, solid juicy, creamy-white flesh, and a unique and distinctive taste embracing the best high qualities of both of its parent varieties, its ability to bear regular and annual crops, its bushy dense foliage, its ability to bear attractive overall reddish fruits on golden-yellow ground and the keeping ability of its fruits.

* * * * *